Figure 1:
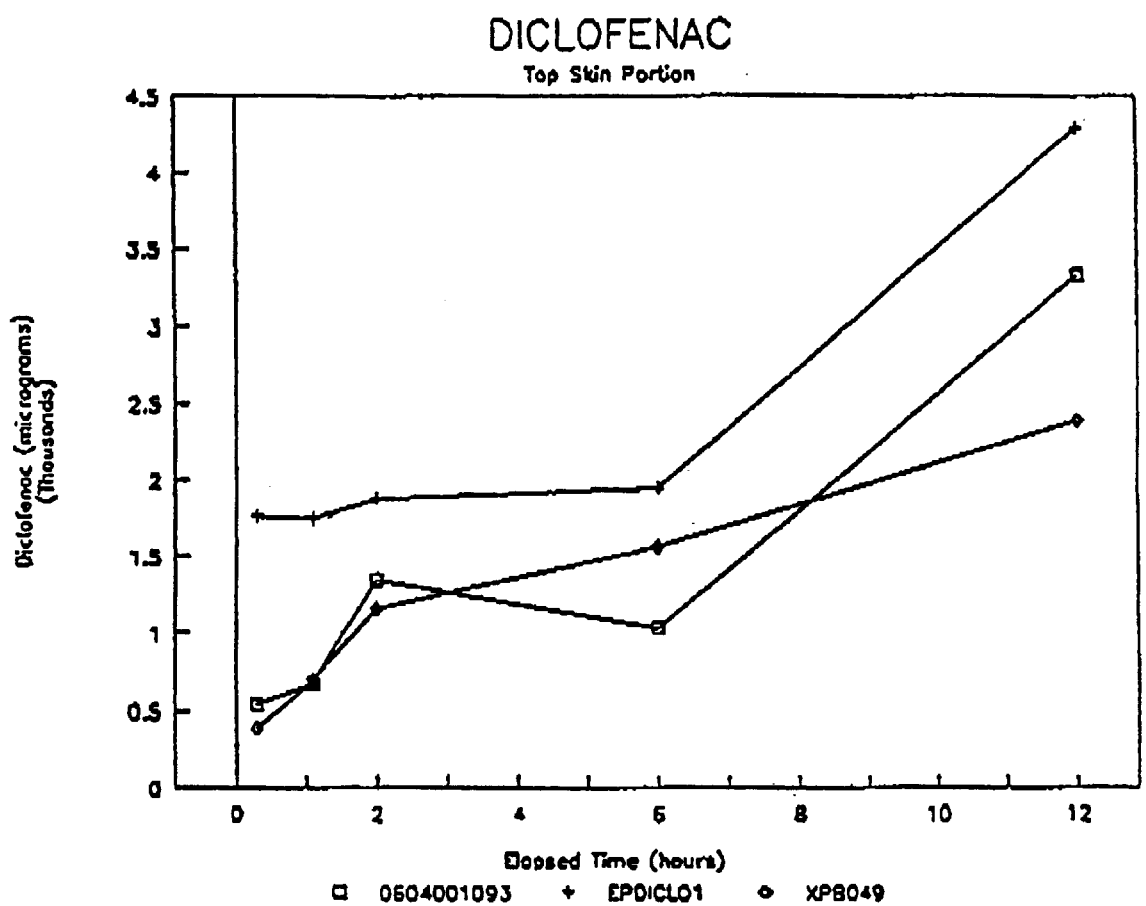

United States Patent [19]
Falk et al.

[11] Patent Number: 6,114,314
[45] Date of Patent: *Sep. 5, 2000

[54] FORMULATIONS CONTAINING HYALURONIC ACID

[75] Inventors: Rudolf Edgar Falk; Samuel Simon Asculai, both of Toronto, Canada; Ehud Shmuel Klein, Givat Savyon, Israel; David W. Harper, Oakville, Canada; David Hochman, Thornhill, Canada; Don Purschke, Toronto, Canada

[73] Assignee: Hyal Pharmaceutical Corp., Canada

[*] Notice: This patent is subject to a terminal disclaimer.

[21] Appl. No.: 08/352,697

[22] Filed: Dec. 1, 1994

Related U.S. Application Data

[62] Continuation of application No. 07/838,674, Feb. 21, 1992, abandoned, and a continuation-in-part of application No. 07/675,908, filed as application No. PCT/CA90/00306, Sep. 18, 1990.

[51] Int. Cl.[7] .................................................. A61K 31/70
[52] U.S. Cl. ........................ 514/54; 514/62; 536/55.1
[58] Field of Search ........................ 514/54, 53; 524/62; 536/55.1

[56] References Cited

U.S. PATENT DOCUMENTS

| | | | |
|---|---|---|---|
| 4,141,973 | 2/1979 | Balazs | 514/54 |
| 4,303,676 | 12/1981 | Balazs | 424/359 |
| 4,582,865 | 4/1986 | Balazs et al. | 524/29 |
| 4,636,524 | 1/1987 | Balazs et al. | 514/781 |
| 4,684,627 | 8/1987 | LeVeen et al. | 514/25 |
| 4,711,780 | 12/1987 | Fahim | 424/145 |
| 4,725,585 | 2/1988 | Wenge et al. | 514/54 |
| 4,736,024 | 4/1988 | Della Valle et al. | 536/55.3 |
| 4,755,544 | 7/1988 | Makino et al. | 524/42 |
| 4,795,741 | 1/1989 | Leshchiner et al. | 514/21 |
| 4,801,619 | 1/1989 | Lindblad | 514/825 |
| 4,808,576 | 2/1989 | Schultz et al. | 514/54 |
| 4,814,176 | 3/1989 | Makino et al. | 424/457 |
| 4,840,941 | 6/1989 | Ueno et al. | 514/29 |
| 4,851,521 | 7/1989 | della Valle et al. | 536/55.1 |
| 4,937,254 | 6/1990 | Sheffield et al. | 514/420 |
| 4,946,870 | 8/1990 | Partain, III et al. | 514/777 |
| 4,957,744 | 9/1990 | della Valle et al. | 524/401 |
| 4,965,353 | 10/1990 | della Valle et al. | 536/55.1 |
| 4,970,298 | 11/1990 | Silver et al. | 536/356 |
| 5,095,037 | 3/1992 | Iwamitsu et al. | 514/561 |
| 5,166,331 | 11/1992 | Fidia | 536/55.1 |
| 5,639,738 | 6/1997 | Falk et al. | 514/54 |

FOREIGN PATENT DOCUMENTS

| | | |
|---|---|---|
| 15456/88 | 9/1988 | Australia . |
| 29145/89 | 6/1989 | Australia . |
| 14534/88 | 11/1990 | Australia . |
| 17459/88 | 8/1991 | Australia . |
| 1205031 | 5/1986 | Canada . |
| 1240929 | 8/1988 | Canada . |
| 2031880 | 12/1990 | Canada . |
| 769 287 | 3/1957 | European Pat. Off. . |
| 0 318 572 | 4/1985 | European Pat. Off. . |
| 0 179 442 | 4/1986 | European Pat. Off. . |
| 0 197 718 | 10/1986 | European Pat. Off. . |
| 0 208 623 | 1/1987 | European Pat. Off. . |
| 0 216 453 | 4/1987 | European Pat. Off. . |
| 0 244 178 | 4/1987 | European Pat. Off. . |
| 0 224 987 | 6/1987 | European Pat. Off. . |
| 0 240 098 | 10/1987 | European Pat. Off. . |
| 0 265 116 | 4/1988 | European Pat. Off. . |
| 0 270 317 | 6/1988 | European Pat. Off. . |
| 0 285 357 | 10/1988 | European Pat. Off. . |
| 0 287 210 | 10/1988 | European Pat. Off. . |
| 0 295 092 | 12/1988 | European Pat. Off. . |
| 0 296 740 | 12/1988 | European Pat. Off. . |
| 0 312 208 | 4/1989 | European Pat. Off. . |
| 0 341 745 | 5/1989 | European Pat. Off. . |
| WO 88/07060 | 9/1988 | WIPO . |
| WO 89/07932 | 9/1989 | WIPO . |

OTHER PUBLICATIONS

Sandra Blakeslee, "Solid cores of tumors keeping out best drugs", Jul. 8, 1989 edition of the Globe and Mail, Toronto, Ontario p. D4.

Pam Harrison, "Toxic drug tamed but still potent" *Ontario Medicine*, vol. 8, No. 16 dated Aug. 21, 1989, Page 1.

*The Merck Index* Eleventh Edition, Centennial Edition, Hyaluronic Acid formulation, pp. 751 and 752.

Alan R. Liss, Inc., Modulation of Immunity in Cancer Patients by Prostaglandin Antagonists, *Immunity to Cancer II*.

Goodwin, J.S. Prostaglandin E and Cancer Growth Potential for Immunotherapy with Prostaglandin Synthesis Inhibitors, *Augmentive Agents in Cancer Therapy*, Raven Press, New York, (1981).

Dr. Samuel Asculai, "*Inactivation of Herpes Simplex Viruses by Nonionic Surfactants*", Antimicrobial Agents and Chemotherapy, Apr. 1978, pp. 686–690.

Chemical Abstracts, vol. 76, No. 10; W. E. Sneader; "Possible Mechanism for action of DMSO on Percutaneous absorption", J. Pharm. Pharmcol, 1971, 23 (Supp).

*Primary Examiner*—Elli Peselev
*Attorney, Agent, or Firm*—Fish & Richardson P.C.

[57] ABSTRACT

Topically applied transdermally quick penetrating (best targeting the epidermis and subsequently remaining there for a prolonged period of time) systemic independent acting, combinations and formulations which employ, combine, or incorporate a therapeutically effective non-toxic (to the patient) amount of a drug which inhibits prostaglandin synthesis together with an amount of hyaluronic acid and/or salts thereof (for example the sodium salt) and/or homologues, analogues, derivatives, complexes, esters, fragments, and/or sub units of hyaluronic acid to treat a disease and condition of the skin and exposed tissue for example, basal cell carcinoma, the precancerous, often recurrent, actinic keratoses lesions, fungal lesions, "liver" spots and like lesions (found for the most part in the epidermis), squamous cell tumours, metastatic cancer of the breast to the skin, primary and metastatic melanoma in the skin, genital warts cervical cancer, and HPV (Human Papilloma Virus) including HPV of the cervix, psoriasis (both plaque-type psoriasis and nail bed psoriasis), corns on the feet and hair loss on the head of pregnant women and remain in the skin for a prolonged period of time.

19 Claims, 3 Drawing Sheets

FORMULATIONS CONTAINING HYALURONIC ACID

This application is a continuation of U.S. application Ser. No. 07/838,679, filed Dec. 21, 1992, now abandoned, which is a continuation-in-part application of U.S. patent application Ser. No. 07/675,908, filed on Jul. 3, 1991 which Application and its contents are incorporated herein by reference in its entirety and which Application was the Application entering the National Phase in the United States from PCT Application Serial No. PCT/CA90/00306, filed Sep. 18, 1990 which Application claims priority from Canadian Patent Application Serial No. 612,3074 filed Sep. 21, 1989.

FIELD OF INVENTION

This invention relates to the treatment of disease and conditions of the skin and exposed tissue. In some embodiments this invention finds application to the treatment of a disease or condition of the skin and exposed tissue including (basal cell carcinoma, squamous cell tumours, metastatic cancer of the breast to the skin, primary and metastatic, melanoma in the skin, genital warts (condyloma acuminata), cervical cancer, HPV (Human Papilloma Virus) including HPV (Human Papilloma Virus) on the cervix, psoriasis (both plaque-type psoriasis and nail bed psoriasis), corns on the feet, and actinic keratoses lesions, "liver" spots, fungal lesions, and other such types of lesions, and hair loss on the head of pregnant women.)

This invention also relates to formulations suitable for use in such treatments, the use of such formulations in such treatments, methods of such treatment, and the delivery of drugs for such treatments.

BACKGROUND OF THE INVENTION

Basal cell carcinoma is presently treated by surgery. Each lesion, together with all surrounding and underlying tissue (dermis, epidermis, and subdermis), is cut out. In some instances, surgery, while necessary for the patient's welfare, may put the patient at risk in some other respect (for example, a lesion on a patient's temple whose removal (resection) may jeopardize the patient's health). Squamous cell tumours are also treated the same way as are other forms of cancer in the skin and exposed tissue. Furthermore, other conditions and diseases of the skin and exposed tissue are treated the same way or in ways that cause discomfort to the patient, for example melanoma, genital warts, cervical cancer, HPV (Human Papilloma Virus).

Actinic keratoses lesion is dealt with similarly. Additionally, liquid nitrogen has been used to remove the lesion.

These diseases and conditions are usually found in the epidermis (at least for the most part extending into the dermis and through Stratum Corneum).

Hyaluronic acid is a naturally occurring glycosaminoglycan. Its molecular weight may vary from 50,000 dalton upwards, and it forms highly viscous solutions. As regards the actual molecular weight of hyaluronic acid in natural biological contexts, this is still a matter of much uncertainty; when the molecular weight of hyaluronic acid is to be determined, different values are obtained depending on the assay method employed, and on the source, the isolation method etc. The acid occurs in animal tissue, e.g. spinal fluid, ocular fluid, synovial fluid, cockscombs, skin, and also in some streptococci. Various grades of hyaluronic acid have been obtained. A preparation with an allegedly high degree of purity and alleged to be entirely free from side effects, is a non-inflammatory form described in U.S. Pat. No. 4,141,973; this preparation is said to have a molecular weight exceeding 750,000 dalton, preferably exceeding 1,200,000 dalton and is suggested for therapeutic use in various articular conditions.

U.S. Pat. No. 4,801,619 relates to hyaluronic acid, having a molecular weight of about $3 \times 10^6$ dalton or more, administered intra-articularly which is prone to decrease the proteoglycan content of synovial fluid to almost normal levels. According to this patent, this indicates a positive effect on the proteoglycan metabolism of a joint. According to the patent, this is applicable both to inflammatory conditions and to degeneration caused by treatment with symptomatics, such as corticosteroid preparations. It is thus clear that a sufficiently high molecular weight of the hyaluronic acid is alleged to counteract side effects that might be caused by corticosteroids or other symptomatics producing similar effects. When corticosteroids are applied, the amount of hyaluronic acid in the synovial cavity will, according to the patent, increase substantially and, according to the inventors, their hyaluronic acid preparations have a very positive effect on such clinical symptoms as pain, swelling, and lameness.

The patent states that the objectives of the invention are attained by intra-articular administration of an effective amount of hyaluronic acid with a mean molecular weight exceeding $3 \times 10^6$ dalton, preferably exceeding $4 \times 10^6$ dalton; usually the molecular weight will not exceed $7 \times 10^6$ dalton. The dosage of hyaluronic acid administered is stated to be preferably within the range of 5 mg–80 mg. The amount of solution given at each administration is generally less than 60 ml, e.g. less than 20 ml. of an aqueous solution of the acid or its salt. It is convenient to administer the acid dissolved in water (<2% w/w, buffered to physiological pH), for instance in the form of a water-soluble sodium salt. The exact amount will depend on the particular joint to be treated.

The Merck Index Specifies that Hyaluronic Acid has a Molecular Weight within the range pf 50,000 to $8 \times 10^6$ depending on source, methods of preparation, and methods of determination. The Merck Publication teaches hyaluronic acid as a surgical aid (ophthalmological).

U.S. Pat. No. 4,808,576 purports to teach that hyaluronic acid, an agent well known for reducing the sequelae of trauma in mammalian joint tissue when applied directly to the traumatized tissue, will be carried to such traumatized tissue by the mammal's natural processes if applied at a site remote from the traumatized tissue. Thus, hyaluronic acid in any therapeutically acceptable form can, according to the Patent, be administered by the typical remote routes including intravenous, intramuscular, subcutaneous, and topical.

This, the patent alleges, makes the utilization of hyaluronic acid much more convenient and attractive. For instance, the treatment of arthritis in horse or human joints with hyaluronic acid, according to the patent, no longer requires more difficult intra-articular injections.

U.S. Pat. No. 4,725,585 relates to a method of enhancing or regulating the host defence of a mammal, said method comprising administering to a mammal a therapeutically effective amount of hyaluronic acid.

At column 1, lines 43–46, the patent provides that the invention was based on the unexpected discovery that administration of hyaluronic acid to mammals results in a considerable increase in the defence.

The hyaluronic acid employed in the patent was Healon provided by Pharmacia AB, Uppsala, Sweden (Pharmacia AB is also entitled to the benefit of U.S. Pat. No. 4,141,973). The patent provides at column 4, line 19 that because a patient's infections had been hard to treat, instead of just hyaluronic acid being administered to the patient to increase the patient's defence, the patient was given hyaluronic acid and an antibiotic. While the patent states that the antibiotic was given in combination with hyaluronic acid, in fact because the hyaluronic acid was administered subcutaneously and because the patient was a heart patient, one skilled in the art would understand that any antibiotic administered, while possibly administered simultaneously was definitely administered separately intravenously (probably) or intramuscularly (less probably). Thus, (most probably) the hyaluronic acid administered, according to the teachings of this patent, was administered in order to prevent possible development of infections (increase the host's defence) and not for any other reason.

U.S. Pat. No. 4,636,524 discloses cross-linked gels of hyaluronic acid, alone and mixed with other hydrophilic polymers and containing various substances or covalently bonded low molecular weight substances and processes for preparing them. These products are alleged to be useful in numerous applications including cosmetic formulations and as drug delivery systems.

The patent further states that as hyaluronic acid is known to be a biologically tolerable polymer in the sense that it does not cause any immune or other kind of response when introduced into a human body, the cross-linked hyaluronic acid gels can be used for various medical applications. The cross-linked gels modified with other polymers or low molecular weight substances, it is alleged, can be used as drug delivery devices. For example, the inventors are alleged to have found that heparin introduced in a cross-linked hyaluronic acid gel retained its antithrombogenic activity.

The inventors also allege that they have also found that cross-linked gels of hyaluronic acid can slow down the release of a low molecular weight substance dispersed therein but not covalently attached to the gel macromolecular matrix.

U.S. Pat. No. 4,736,024 purports to teach new medicaments for topical use containing:

(i) an active pharmacological substance or a mixture of pharmacological substances, either active or suitable for topical administration and (ii) a topical vehicle which comprises hyaluronic acid or a molecular fraction of hyaluronic acid or a salt of the same with an alkaline metal, an alkaline earth metal, magnesium, aluminium, ammonium, or a pharmacological substance optionally together with additional conventional excipients for pharmaceutical preparations for topical use.

Applicants are also aware of published Japanese Patent Document 61000017, dated 86/01/06, whose English abstract of disclosure states that the Japanese Patent Document relates to the use of hyaluronic acid or cross-linked hyaluronic acid or their salts as the active ingredient for inhibiting carcinoma metastasis.

According to the purported abstract of the patent, more that 1.0% of hyaluronic acid is dissolved in alkaline aq. soln. and pref. more than 50% of $H_2O$ sol. org. solvent. eq. alcohol, acetone, dioxane, against total soln. is added. Preferably the pH is 12–14. Then multifunctional epoxy cpd. is added and reacted at 10–60 deg. C., pref. at 20–40-deg. C. for 24 hrs. Cross-linking ratio of crosslinked hyaluronic acid or its salt is regulated by changing mol ratio of hyaluronic acid or its salt and multifunctional epoxy cpd. Pref. hyaluronic acid used has intrinsic viscosity 0.2–30,m.w. 4000–2000000. The hyaluronic acid is allegedly used in several dosage forms. Clinical dose for adult is alleged to be normally, as hyaluronic acid or cross-linked hyaluronic acid, 25 mg-5 g/day (p.o.) and 10 mg-2.5 g/l dose (inj). The abstract alleges that the advantage is that the hyaluronic acid has no side effects as may other anti-cancer drugs and has an analgesic and a tissue restoration effect.

European Patent Application 0295092 purports to teach a vehicle together with fragments of hyaluronic acid for delivering of the fragments of hyaluronic acid into the skin to reach the dermal layer of the skin to increase the development of blood vessels for stimulating hair growth or regrowth. The preferred fragments of hyaluronic acid are polysaccharides containing from 7 to 25 monosaccharide units. The patent provides that it is apparent that the larger the fragments of hyaluronic acid, the greater the difficulty there is in delivering the fragments to the dermal layer of the skin, unless there is also present in the composition a means for enhancing the activity of said fragments.

The combination may thus include a means for enhancing the activity of the fragments of hyaluronic acid, especially to improve their penetration through the skin following topical application. Some activity enhancers, it is alleged, also function as vehicles for the fragments of the hyaluronic acid.

Some activity enhancers are also alleged to possess the ability to stimulate or increase hair growth. Minoxidil is asserted among others to be such an activity enhancer. Thus both the fragments of hyaluronic acid and minoxidil are alleged to stimulate hair growth both delivered by a vehicle.

European Patent Application 0179442 asserts that where free radicals are formed in considerable quantities, hyaluronic acid is broken down or degraded before the hyaluronic acid has given the desired effect.

Canadian Letters Patent 1,240,929 teaches the combination of chondroitin sulfate compound and a hyaluronate to protect both human and animal cell layers and tissue subject to exposure to trauma.

European Patent Application 0208623 purports to teach hyaluronic acid as "une augmentation de l'activité de certaines proteases". It also purports to teach the use of hyaluronic acid for treating connective tissue diseases, including malignant tumours and cardiovascular disorders.

European Patent Application 270317 purports to teach the combination of an antiviral agent lacking inhibitory action and a compound [for example, hyaluronic acid] possessing cell fusion inhibitory activity and/or virus-adsorption inhibitory activity for treating disease carried by a virus.

U.S. Pat. No. 4,840,941 purports to teach the use of an effective amount of hyaluronic acid as the active agent for the treatment of retroviruses in association with a pharmaceutically acceptable carrier, diluent, or excipient.

U.S. Pat. No. 4,851,521 and European Patent Application 0265116 both describe hyaluronic acid fractions, the making thereof and cross-linked esters of hyaluronic. U.S. Pat. No. 4,851,521 describes esters of hyaluronic acid incorporated into pharmaceutical preparations as the active ingredient and as vehicles for ophthamological medicines for topical use (See column 11, lines 35 to 42; and column 12, lines 62 to column 13, line 3) and in suppositories for a systemic effect due to the effect of transcutaneous absorption, such as in suppositories.

The patent provides at column 13, lines 5 to 31: "The vehicling action of the hyaluronic esters also applies to associated medicaments of the type mentioned above in which the active substance acts not only topically or by nasal or rectal absorption, for example by nasal sprays or preparations for inhalation for the oral cavity or the pharynx, but also by oral or parenteral route, for example by intramuscular, subcutaneous or intravenous route, as it favors absorption of the drug into the application site. The new medicaments can therefore be applied, apart from in the fields already mentioned, in practically all sectors of medicine, such as internal medicine, for example in pathologies of the cardiovascular system, in infections of the respiratory system, the digestive system, the renal system, in diseases of an endocrinological nature, in oncology, in psychiatry etc., and may also be classified therefore from the point of view of their specific action, being perhaps anesthetics, analgesics, anti-inflammatories, wound healers, antimicrobics, adrenergic agonsits and antagonists, cytostatics, antirheumatics, antihypertensives, diuretics, sexual hormones, immunostimulants and immunosuppressants, for example, one of the drugs having the activity already described for the therapeutically active alcohols to be used as esterifying component according to the present invention, or for the therapeutically active bases used for the salification of the free carboxylic groups."

There have been extensive studies to determine the defect in immune function that allows a tumour cell to develop. It was postulated initially by Jerne, and subsequently by Burnett, that the immune system's major role was that of immunological surveillance to destroy abnormal cells. The concept of surveillance, while somewhat simplistic, remains an accepted concept for the elaborate mechanism of immune recognition and function that is present in the higher species—mammals.

It has then been postulated that tumours develop because of local or generalized immune suppression. However, as pointed out by Moller, if general immune suppression occurs, it is only certain types of neoplastic disorders that develop, mainly those of the lympho-reticular system. This observation is correct and represents a major challenge to the immune surveillance theory unless a specific reason can be shown as to why the individual cancer cell can develop plus individually evade the immune system.

It was demonstrated experimentally in 1974 that defects of macrophage function may exist in neoplastic disease.

The initial experiments found suppressor cells to be part of the immune system; these were either of the T-cell type of the macrophage cell system. There was presence demonstrated in neoplasia, chronic bacterial infection, recovery from massive injury and chronic fungal infection.

There has been repeated demonstration in experimental animals that the macrophage cell function is altered in neoplastic disease. The macrophages in the animal's systems appeared "blocked" in their function. Generally when removed from the in vivo situation, washed in saline and cultured, they could perform normally. This block has been shown to be related to the excessive production of prostaglandin by neoplastic tissue or by the macrophage itself. Similarly, the N.K. cells (which are said to be primitive or immature macrophages and which may be involved in cancer defence) are also blocked.

In the basic research efforts in the latter '70s and the early '80's, there existed considerable confusion as to what role immunotherapy should take in cancer. Activation or "hyping" of macrophages was thought to be important. However, in an examination by Romans and Falk of peritoneal macrophages obtained from patients with neoplastic disease, there was definite evidence that these macrophages were already activated yet were co-existing with cancer cells and not causing their destruction.

It has recently been shown by several independent investigators that the malfunction of macrophages or the putitive block is due to excessive prostaglandin and that this can be altered in tissue culture by corticosteroids, ASA, and the non-steroidal anti-inflammatory drugs, i.e. indomethacin and naproxen (Naprosyn™). Again, it was repeatedly demonstrated that in animal tumours these substances could alter the response to neoplastic cells and that various combinations of these substances employed with immune enhancing agents could produce very credible success in eliminating experimental tumours. Lala and co-workers combined Indomethacin therapy with Interleukin 2 and showed that this could effect a cure with experiment neoplasm.

There were continued problems with the use of any of these agents in the actual human in vivo experience. All of the non-steroidal anti-inflammatory agents (NSAID) produced major toxicity in terms of gastro-intestinal, neurological, and other areas. Thus, the basis of the present approach is that, under general circumstances, with the use of these agents in human disease in sufficient amounts, the drug will penetrate to any pathological tissue to alter therapeutically local prostaglandin production. While intravenous preparations of Indomethacin (and now of other agents) exist, using these drugs alone produces prohibitive side effects in human subjects. Therefore, only insufficient amounts can be brought into the body to effect more than occasional responses in neoplasm.

However, the majority of the evidence is present to indicate and therefore, it can be postulated that the basis for neoplastic development and how the initial cell "sneaks by" the immune surveillance mechanism relates to its production of prostaglandin. One need postulate only one mutation to alter the amount of prostaglandin synthesis produced by cells when they become "malignant" to establish a mechanism of blocking out the initial cell in any immune reaction, i.e. the macrophage. It therefore became essential to develop a combination of NSAIDs for clinical use to produce a major improvement in response in neoplastic disease and other conditions where excessive prostaglandin synthesis represents the basis of the pathogenesis of this disease state, i.e. arthritis and various others of the so-called connective tissue inflammatory disorders and/or auto-aggressive diseases.

See also:

1. Modulation of Immunity in Cancer Patients by Prostaglandin Antagonists, *Immunity to Cancer II*, Alan R. Liss, Inc.; and
2. Goodwin, J. S., (1981) Prostaglandin E and Cancer Growth Potential for Immunotherapy with Prostaglandin Synthesis Inhibitors, *Augmentive Agents in Cancer Therapy*, Raven Press, New York.

U.S. Pat. No. 4,711,780 teaches a pharmaceutical composition comprising Vitamin C, a zinc salt, and a sulfur amino acid for treating surface epithelium for epithelium regeneration. Hyaluronic acid may be added for applications in the reproductive tract.

Because of the side effects of the use of non-steroidal anti-inflammatory drugs (major toxicity in terms of gastro-intestinal, neurological, and other areas),use thereof should also be restricted (if possible) to the area of use without delivery to other areas which are not in need of treatment. Thus, if useful amounts of the non-steroidal anti-inflammatory drugs could be delivered to a site in need thereof without carriage of substantial amounts away from the site to be treated, then the use of a non-steroidal anti-inflammatory drug may have many other useful applications.

SUMMARY OF THE INVENTION

Applicants have now discovered that topically applied transdermally quick penetrating (best targeting the epidermis and subsequently remaining there for a prolonged period of time) combinations and formulations which employ, combine, or incorporate (as the case may be) a therapeutically effective non-toxic (to the patient) amount of a drug which inhibits prostaglandin synthesis, preferably a non-steroidal anti-inflammatory drug (NSAID), for example, diclofenac, indomethacin, naproxen, and (±) tromethamine salt of ketorolac (sold under the trademark Toradol™) together with an amount of hyaluronic acid and/or salts thereof (for example the sodium salt) and/or homologues, analogues, derivatives, complexes, esters, fragments, and/or sub units of hyaluronic acid (preferably hyaluronic acid and salts thereof), may be used to treat the disease and condition of the skin and exposed tissue for example, basal cell carcinoma, the precancerous, often recurrent, actinic keratoses lesions, fungal lesions, "liver" spots and like lesions (found for the most part in the epidermis), squamous cell tumours, metastatic cancer of the breast to the skin, primary and metastatic melanoma in the skin, genital warts (condyloma acuminata) cervical cancer, and HPV (Human Papilloma Virus) including HPV of the cervix, psoriasis (both plaque-type psoriasis and nail bed psoriasis), corns on the feet and hair loss on the head of pregnant women, with dramatic success. Furthermore, application of the combinations and formulations are systemic independent (there is a lack of a blood level of the NSAID), quick to penetrate into the skin particularly to the epidermis and remain there for prolonged periods.

Thus, according to one aspect of the invention, Applicants have provided topically applied transdermally penetrating (best targeting the epidermis) systemic independent acting (not acting essentially through the blood) pharmaceutical combinations and formulations comprising, together with pharmaceutical excipients suitable for topical application, a therapeutically effective (to treat and resolve the disease and conditions of the skin and exposed tissue (for example basal cell carcinoma, the precancerous, often recurrent, actinic keratoses lesions, fungal lesions, "liver" spots and like lesions (found for the most part in the epidermis), squamous cell tumours, metastatic cancer of the breast to the skin, primary and metastatic melanoma in the skin, genital warts (condyloma acuminata) cervical cancer, and HPV (Human Papilloma Virus) including HPV of the cervix, psoriasis (both plaque-type psoriasis and nail bed psoriasis), corns on the feet and hair loss on the head of pregnant women), non-toxic (to the patient) amount of a drug which inhibits prostaglandin synthesis, preferably a non-steroidal anti-inflammatory drug (NSAID), for example, diclofenac, indomethacin, naproxen, and (+,−) tromethamine salt of ketorolac (sold under the trademark Toradol™) administered with, or carried in, an amount of hyaluronic acid and/or salts thereof (for example, the sodium salt) and/or homologues, analogues, derivatives, complexes, esters, fragments, and/or sub-units of hyaluronic acid (preferably hyaluronic acid and salts thereof) sufficient to facilitate the NSAID's quick penetration to the site in the skin (for example epidermis) or tissue of the disease or condition through the tissue to remain there for a prolonged period of time to block prostaglandin synthesis. This blockage of prostaglandin synthesis then unblocks the macrophages and permits the macrophages of the patient proximate the lesion (for example, the basal cell carcinoma) to destroy the lesion or condition. Treatment with the formulation and combination eliminates the condition without recurrence, even where the lesion has recurred a number of times after other unsuccessful treatments. Other non-steroidal anti-inflammatory drugs may be used such as other propionic acid derivatives, Ibuprofen, acetylsalicylic acid, piroxicam and flunixin.

When such combinations and formulations are applied to the site of the disease or condition for example the basal cell carcinoma of the patient suffering from, the basal cell carcinoma over a period of time (for example, for a period of 2–4 weeks 3 times daily) the basal cell carcinoma is completely resolved and disappears.

According to another aspect of the invention, a method of treating a disease or condition of the skin or exposed tissue for example basal cell carcinoma, the precancerous, often recurrent, actinic keratoses lesions, fungal lesions, "liver" spots and like lesions (found for the most part in the epidermis), squamous cell tumours, metastatic cancer of the breast to the skin, primary and metastatic melanoma in the skin, genital warts (condyloma acuminata) cervical cancer, and HPV (Human Papilloma Virus) including HPV of the cervix, psoriasis (both plaque-type psoriasis and nail bed psoriasis), corns on the feet and hair loss on the head of pregnant women, in a mammal is provided comprising administering topically to the mammal a combination comprising, together with pharmaceutical excipients suitable for topical application, a therapeutically effective (to treat and resolve the disease or condition for example basal cell carcinoma or other lesion), non-toxic (to the patient) amount of a drug which inhibits prostaglandin synthesis, preferably a non-steroidal anti-inflammatory drug (NSAID), for example, diclofenac, indomethacin, naproxen, and (+,−) tromethamine salt of ketorolac (sold under the trademark Toradol™) administered with, or carried in, an amount of hyaluronic acid and/or salts thereof (for example, the sodium salt) and/or homologues, analogues, derivatives, complexes, esters, fragments, and/or sub-units of hyaluronic acid (preferably hyaluronic acid and salts thereof) sufficient to facilitate the drug's (for example NSAID's) penetration to the site in the skin of the disease or condition to be treated through the tissue (including any scar tissue) at the site through the cell membrane, thereby blocking prostaglandin synthesis.

Thus, according to another aspect of the invention, the treatment may employ the use of the formulation or combination by applying the formulation or combination a number of times daily (for example, 3 times daily) for a period of time, for example, 2–4 weeks to clear the lesion.

One such formulation may comprise 3% diclofenac in a 2½% hyaluronic acid (sodium hyaluronate—molecular weight 661,600) gel formulation, with the excipients being glycerine (5%), benzyl alcohol (3%) (acting in part as a solubilizer and preservative), and sterile water (the balance).

Another such formulation may comprise 3% diclofenac in a 2½% hyaluronic acid (sodium hyaluronate—molecular weight 679,000) gel formulation with excipients being benzyl alcohol (1%) (a preservative), methoxypolyethylene glycol 350 (20%) (a solubilizer), and sterile water (the balance).

While the above formulations are suggested, provided these is sufficient hyaluronic acid (for example, sodium hyaluronate) to facilitate the penetration to the site in the skin (for example epidermis) of a sufficient amount of a drug which inhibits prostaglandin synthesis, preferably an NSAID (for example, diclofenac), to block prostaglandin synthesis, then the formulations may be of any suitable form, for example, a 1% lotion of hyaluronic acid, or cream or any suitable combination.

While higher molecular weights of the hyaluronic acid and forms thereof may be used and may penetrate more rapidly, where the molecular weight of the hyaluronic acid chosen for use is very large, there may not be as much penetration. Thus, the hyaluronic acid may be autoclaved, to break down the hyaluronic acid to fragments of lesser molecular weight. Furthermore, because there is little concern with respect to the toxicity or adverse effects with the use of, for example, the NSAIDs with the hyaluronic acid, after solubilizing the NSAID in a suitable solubilizer, the NSAID may be combined as needed.

According to another aspect of the invention, transdermal delivery of a therapeutically effective amount of a drug which inhibits prostaglandin synthesis, preferably a non-steroidal drug (NSAID) to the site in the skin to treat a disease or condition for example the basal cell carcinoma (or actinic keratoses lesion) in a mammal is provided, the delivery comprising topically administering (to for example the basal cell carcinoma or other lesion) a therapeutically effective non-toxic (to the patient) amount of an agent which inhibits prostaglandin synthesis, preferably an NSAID (non-steroidal anti-inflammatory drug), for example, diclofenac, indomethacin, naproxen, and (±) tromethamine salt of ketorolac (sold under the trademark Toradol™), with a sufficient amount of hyaluronic acid and/or salts thereof and/or homologues, analogues, derivatives, complexes, esters, fragments, and sub-units of hyaluronic acid, preferably hyaluronic acid and salts thereof, sufficient to transport, or facilitate the transport of, the NSAID to the site of the disease or condition usually in the epidermis, for example the basal cell carcinoma (or other lesion) through the cell membranes into the individual cells to be treated to block the synthesis of prostaglandins.

Thus, according to another aspect of the invention, use of a combination or formulation is provided to treat the disease or condition for example the basal cell carcinoma (or other lesion), the combination and formulation comprising together with pharmaceutical excipients suitable for topical application, a therapeutically effective (to treat and resolve, for example, the basal cell carcinoma), non-toxic (to the patient) amount of an agent which inhibits prostoglandin synthesis preferably a non-steroidal anti-inflammatory drug (NSAID), for example, diclofenac, indomethacin, naproxen, and (+,−) tromethamine salt of ketorolac (sold under the trademark Toradol™) administered with, or carried in, an amount of hyaluronic acid and/or salts thereof (for example, the sodium salt) and/or homologues, analogues, derivatives, complexes, esters, fragments, and/or sub-units of hyaluronic acid (preferably hyaluronic acid and salts thereof) sufficient to facilitate the NSAID's penetration into the skin especially the epidermis through the tissue (including any scar tissue) at the site of the disease or condition for example basal cell carcinoma (or other lesion) to be treated, thereby blocking prostaglandin synthesis to enable the macrophages (and N.K. cells) to resolve the disease or condition for example basal cell carcinoma or other lesion.

Applicants postulate that the hyaluronic acid and/or salts thereof and/or the homologues, analogues, derivatives, complexes, esters, fragments, and/or sub units of hyaluronic acid facilitate the transport of the agent (preferably NSAID) to the site of prostaglandin synthesis to block prostaglandin synthesis and, at the same time, abate the pain the patient is experiencing at the paccinian nerve bundles (superficial nerve bundles).

By way of example and to illustrate the facilitation of the delivery or transport of a chemical to a site in a mammal, when ethyl alcohol is injected directly into a tumour and sonographic (ultrasound) assessment is made, it is not dispersed throughout the tumour. When the ethyl alcohol to be administered into a tumour is carried by hyaluronic acid and/or salts thereof, sonographic assessment of the tumour demonstrates the dispersion of the ethyl alcohol throughout the tumour.

While Applicants postulate that the hyaluronic acid facilitates the transport and delivery, Applicants' invention may be used as described irrespective of the actual method of operation of the hyaluronic acid and/or salts thereof and/or the homologues, analogues, derivatives, complexes, esters, fragments and sub-units of hyaluronic acid.

The combination of hyaluronic acid and salts thereof and other forms with drugs that inhibit prostaglandin synthesis, for example NSAIDs, alters their distribution and performance in the human body, permitting amounts of NSAIDs to be used that could otherwise cause severe side effects (because, in part, the combinations and formulations are systemic independent), and produces an unusual targeting for underperfused tissue and/or pathological tissue.

As a major amount of soluble indomethacin may be required, the chemical product may be solubilized using n-methyl glucamine at a dilution of 5 mg/ml of n-methyl glucamine (NMG). This substance is then passed through a 22 micron Milipore filter to produce sterility. This material is non-toxic at 16 fold the therapeutic dose in animals (with hyaluronic acid) and for this reason was considered appropriate to be used in human conditions. Thus, Indocid™ solubilized in NMG may be administered with hyaluronic acid topically for transdermal penetration at, for example, varying doses. The solution of indomethacin and NMG may be diluted with, for example, "LifeCore™" hyaluronic acid. This produces an appropriate mixture and can be administered safely. (Similar clinical studies have been done with hyaluronic acid prepared by other methods, i.e. extraction.)

When the NSAID, for example indomethacin (dissolved in n-methyl glucamine) or other NSAID, is applied topically in a formulation with the form of hyaluronic acid, no major toxic side effects occur, such as gastro-intestinal distress, neurological abnormalities, depression, etc., even at elevated amounts of indomethacin (if necessary). (This may be in part because of the clearing of the hyaluronic acid through the lymphatic system from the site). In addition, the responses that have been observed are dramatic when the NSAID (for example diclofenac) is combined with hyaluronic acid, demonstrating clearly that the combination is now "targeting" to the pathological tissue. Furthermore, the patients using the formulations and combinations of NSAID—hyaluronic acid (sodium hyaluronate) (for example, diclofenac or indomethacin and hyaluronic acid), experience dramatic relief of pain immediately. Thus, Applicants believe that the use of the NSAID, for example with hyaluronic acid (sodium hyaluronate), deblocks the macrophages (and N.K. cells (Natural Killer Cells) thought to be immature macrophages) by preventing enzymatic production of prostaglandin which blocks macrophage (and N.K. cell) functioning. The hyaluronic acid (and salt and other forms) not only enhances the activity of the NSAID but also reduces any side effects and toxicity that is associated with the use of the prostaglandin synthesis inhibitors. When formulations and combinations of the NSAIDs (for example, diclofenac) with, for example, hyaluronic acid or the sodium salt thereof, are applied to for example the tumour lesion (for example basal cell carcinoma) or other condition (for example, actinic keratoses lesion) for a period of time (for example, 3 times daily for 2–4 weeks), the carcinoma and lesions, as the case may be, disappear.

Applicants also postulate that when the combination or formulation is applied to the disease or condition (for example, basal cell carcinoma or actinic keratoses), the hyaluronic acid passes between the cells (in the stratum corneum, epidermis, and dermis) to the areas deficient in hyaluronic acid (or forms thereof), taking, drawing, carrying or pulling the NSAID with it to the sites of prostaglandin synthesis, penetrating to inhibit prostaglandin synthesis. The NSAID now being proximate the Paccinian nerve bundle (superficial nerve bundles at the end of the nerves) gives pain relief. The macrophages (which have been blocked) are then unblocked and act to destroy the disease or condition for example basal cell carcinoma, actinic keratoses lesion, or other disease or lesion. Furthermore, the combination or formulation, comprising the form of hyaluronic acid and NSAID passing through the stratum corneum, epidermis, and dermis, slowly passes through the skin, staying longer in the skin at the site. Therefore, after having an immediate effect (for example, relieving pain and acting on the basal cell carcinoma, actinic keratoses and other disease, condition or lesion), the NSAID-hyaluronic acid combination remains longer at the site in need of treatment before it is cleared, Applicants believe, through the lymphatic system.

Furthermore, according to another aspect of Applicant's invention, Applicant's formulations and combinations and use of the formulations and combinations quickly penetrates through the stratum corneum into the epidermis (and dermis) where it remains for a prolonged time for treatment.

Fifteen (15) minutes after application of one of Applicants' formulations, about three times the amount of Applicants' formulation has penetrated into the skin (particularly the epidermis) than formulations and combinations not containing hyaluronic acid but containing the same drug. Furthermore, the drug and hyaluronic acid remain at the site for a longer period of time.

Thus according to another aspect of the invention Applicants have provided a formulation and combination comprising together with pharmaceutical excipients suitable for topical application, a therapeutically effective (to treat and resolve the disease and conditions of the skin and exposed tissue (for example basal cell carcinoma, the precancerous, often recurrent, actinic keratoses lesions, fungal lesions, "liver" spots and like lesions (found for the most part in the epidermis), squamous cell tumours, metastatic cancer of the breast to the skin, primary and metastatic melanoma in the skin, gential warts cervical cancer, and HPV (Human Papilloma Virus) including HPV of the cervix, psoriasis (both plaque-type psoriasis and nail bed psoriasis), corns on the feet and hair loss on the head of pregnant women, non-toxic (to the patient) amount of a drug which inhibits prostaglandin synthesis, preferably a non-steroidal anti-inflammatory drug (NSAID), for example, diclofenac, indomethacin, naproxen, and (+,−) tromethamine salt of ketorolac (sold under the trademark Toradol™) administered with, or carried in, an amount of hyaluronic acid and/or salts thereof (for example, the sodium salt) and/or homologues, analogues, derivatives, complexes, esters, fragments, and/or sub-units of hyaluronic acid (preferably hyaluronic acid and salts thereof) sufficient to facilitate the NSAID's quick penetration to the site in the skin (for example epidermis) or tissue of the disease or condition through the tissue to remain there for a prolonged period of time to block prostaglandin synthesis. Thus the formulation or combination penetrates quickly into the skin, for example epidermis of the skin, accumulates there and remains there for a prolonged period of time, thereby accumulating the drug and forms of hyaluronic acid in the skin (particularly the epidermis).

Thus according to another aspect of the invention, a method of accumulating a drug and a form of hyaluronic acid in the skin is provided comprising topically administering together with pharmaceutical excipients suitable for topical application, a therapeutically effective (to treat and resolve the disease and conditions of the skin and exposed tissue (for example basal cell carcinoma, the precancerous, often recurrent, actinic keratoses lesions, fungal lesions, "liver" spots and like lesions (found for the most part in the epidermis), squamous cell tumours, metastatic cancer of the breast to the skin, primary and metastatic melanoma in the skin, genital warts cervical cancer, and HPV (Human Papilloma Virus) including HPV of the cervix, psoriasis (both plaque-type psoriasis and nail bed psoriasis), corns on the feet and hair loss on the head of pregnant women, a non-toxic (to the patient) amount of a drug for example which inhibits prostaglandin synthesis, preferably a non-steroidal anti-inflammatory drug (NSAID), for example, diclofenac, indomethacin, naproxen, and (+,−) tromethamine salt of ketorolac (sold under the trademark Toradol™) administered with, or carried in, an amount of hyaluronic acid and/or salts thereof (for example, the sodium salt) and/or homologues, analogues, derivatives, complexes, esters, fragments, and/or sub-units of hyaluronic acid (preferably hyaluronic acid and salts thereof) sufficient to facilitate the NSAID's quick penetration to the site in the skin (for example epidermis) or tissue of the disease or condition to remain there for a prolonged period of time for example to block prostaglandin synthesis.

According to another aspect of the invention, a method of quickly delivering a drug to the skin, particularly the epidermis, and maintaining the drug therein for a prolonged period of time is provided, the method comprising topically administering together with pharmaceutical excipients suitable for topical application, a therapeutically effective (to treat and resolve the disease and conditions of the skin and exposed tissue (for example basal cell carcinoma, the precancerous, often recurrent, actinic keratoses lesions, fungal lesions, "liver" spots and like lesions (found for the most part in the epidermis), squamous cell tumours, metastatic cancer of the breast to the skin, primary and metastatic melanoma in the skin, genital warts cervical cancer, and HPV (Human Papilloma Virus) including HPV of the cervix, psoriasis (both plaque-type psoriasis and nail bed psoriasis), corns on the feet and hair loss on the head of pregnant women, non-toxic (to the patient) amount of a drug for example which inhibits prostaglandin synthesis, preferably a non-steroidal anti-inflammatory drug (NSAID), for example, diclofenac, indomethacin, naproxen, and (+,−) tromethamine salt of ketorolac (sold under the trademark Toradol™) administered with, or carried in, an amount of hyaluronic acid and/or salts thereof (for example, the sodium salt) and/or homologues, analogues, derivatives, complexes, esters, fragments, and/or sub-units of hyaluronic acid (preferably hyaluronic acid and salts thereof) sufficient to facilitate the NSAID's quick penetration to the site in the skin (for example epidermis) or tissue of the disease or condition through the tissue to remain there for a prolonged period of time (for example epidermis and dermis) to for example block prostaglandin synthesis.

According to another aspect of the invention, a method of controlling the unloading of a drug from the skin or exposed tissue into the lymphatic system comprising delivering into the skin a drug and a form of hyaluronic acid comprising an amount of hyaluronic acid and/or salts thereof and/or homologues, analogues, derivatives, complexes, esters, fragments, and/or sub-units of hyaluronic acid.

We have compared the penetration and retention of one of our combinations (formulations) with a control and Voltarol Emulgel in the skin as follows:

| (A) OUR FORMULATION | | | | |
|---|---|---|---|---|
| 1% DICLOFENAC IN 3.0% HA GEL 50 g/tube | | | | |
| EPDICLO1 | | | | |
| LOT XPB 044 | | | Quantity 1500 ml | |
| FORMULA | Supplier | Lot | Amount | Percent |
| Sterile Water | Baxter | AW45F1 | 1397 ml | — |
| Glycerin | Life | 1043 | 45 g (3.6 ml) | 3% |
| Benzyl Alcohol | Caledon | 02517 | 22.5 g (22 ml) | 1.5% |
| Liquid Wax DICDD | Brooks | 191-175 | 45 g | 3% |
| Diclofenac Sodium | Prosintex | 9113003 | 15 g | 1% |
| Sodium Hyaluronate Mol. Wt. 661,600 | Skymart | HG-1103 | 45 g | 3% |

Procedure

Set up stirring apparatus using a 3 liter stainless steel beaker

Add Water, Glycerin, Benzyl Alcohol and Liquid Wax DICDD, stir and mix for 10 minutes Add Diclofenac Sodium and stir for 30 minutes to dissolve Add Sodium Hyaluronate and stir for 90 minutes Filled In a 50 ml aluminum collapsible tube, inside of tube lacquered with a phanolic resin, outside of tube white regular enamel coating; 9 mm white polypropylene screw on cup with pierce tip

| Gels | | Batch No.s |
|---|---|---|
| (B) | Voltarol Emulgel | 060400 10 93 |
| (C) | 1% Diclofenac Gel | XPBO49 (Control) |
| (C) | CONTROL | |

1% DICLOFENAC IN CARAPOL GEL, 50 g Jar

LOT XPB 049     Quantity 100 ml

| FORMULA | Supplier | Lot | Amount | Percent |
|---|---|---|---|---|
| Sterile Water | Baxter | AW45N5 | 93 ml | — |
| Glycerin | BDH | 2579 | 3 g | 3% |
| Benzyl Alcohol | BDH | 23797 | 1.5 g | 1.5% |
| Liquid Wax DICDD | Brooks | L-1424 | 3 g | 3% |
| Diclofenac Sodium | Prosintex | 9113003 | 1 g | 1% |
| Carbopol 934 | A & C Chemicals | 910304 | 1 g | 1% |

Procedure

Set up stirring apparatus using a 400 ml stainless steel beaker

Add Water, Glycerin, Benzyl Alcohol, Liquid Wax DICDD, and stir to mix thoroughly for 10 minutes Add Diclofenac Sodium and stir for 20 minutes to dissolve Very slowly add Carbopol 934, avoid getting lumps

| Samples Cell | Sample | Quantity of gel applied (mg) |
|---|---|---|
| A | 060400 10 93 | 192 |
| B | 060400 10 93 | 192 |
| C | EPDICLO1* | 192 |
| D | EPDICLO1* | 192 |
| E | XPB049 | 192 |
| F | XPB049 | 192 |

\* - Our Formulation

Skin Type

One piece of skin (Female, 37 years, smoker, breast skin) was used for one sample from each batch. A second piece of skin (no further details available) was used for the second sample from each batch. The skin was stored deep frozen (←−20° C.) until thawed for this experiment. Full thickness skin was used for this experiment.

Experimental Conditions

Skin permeation cells were prepared containing an exposed skin surface area of 9.6 cm$^2$ and a constantly stirred receptor fluid beneath the skin consisting of 135 ml of ethanol:phosphate buffered saline (25:75 v/v).

Each cell was allowed to equilibrate for 1 hour at 37° C. after which the gel was spread evenly over the skin surface at a concentration of 20 mg/cm$^2$). See table above. The cell was then maintained at 37° C. with an air temperature above the skin of 35° C.

24 hours after application of the gel the experiment was stopped and a portion of the receptor fluid removed. The skin was removed from the cell and any gel remaining on the surface carefully wiped off with dry paper towel followed by paper towel moistened with water. The skin was cut with a scalpel to obtain thin top and thicker lower sections of skin.

This was done in order to obtain layers of skin which approximated the epidermal and dermal layers. Each skin section was weighed and the residual diclofenac extracted with 10 ml of fresh receptor fluid using an ultra turrax homogeniser. The homogenates were centrifuged and a portion of the resultant supernatant solutions removed.

The receptor fluid and skin extracts from each cell were assayed for diclofenac content by using a validated reverse phase high performance liquid chromatography (HPLC) method.

Results

Distribution of Diclofenac 24 hours after application of Diclofenac Gel

| | | Top Skin portion | | | Bottom skin portion | | |
|---|---|---|---|---|---|---|---|
| Sample | Receptor μg | Skin Weight (g) | μg | μg/g | Skin Weight | μg | μg/g |
| (Voltarol Emugel) | | | | | | | |
| 060400 10 93 | 447 | 0.1363 | 101 | 742 | 1.2449 | 217 | 174 |
| 060400 10 93 | 764 | 0.2445 | 141 | 577 | 1.2351 | 202 | 164 |
| Mean | 606 | | | 660 | | | 169 |
| (Our Formulation) | | | | | | | |
| EPDICLO1 | 247 | 0.1535 | 133 | 867 | 1.4663 | 148 | 101 |
| EPDICLO1 | 292 | 0.1647 | 145 | 879 | 1.0022 | 86 | 86 |
| Mean | 269 | | | 873 | | | 93 |
| (Control) | | | | | | | |
| XPB049 | 184 | 0.1275 | 35 | 272 | 1.1324 | 58 | 51 |
| XPB049 | 147 | 0.2068 | 82 | 396 | 1.0893 | 68 | 63 |
| Mean | 165 | | | 334 | | | 57 |

Figure 2:
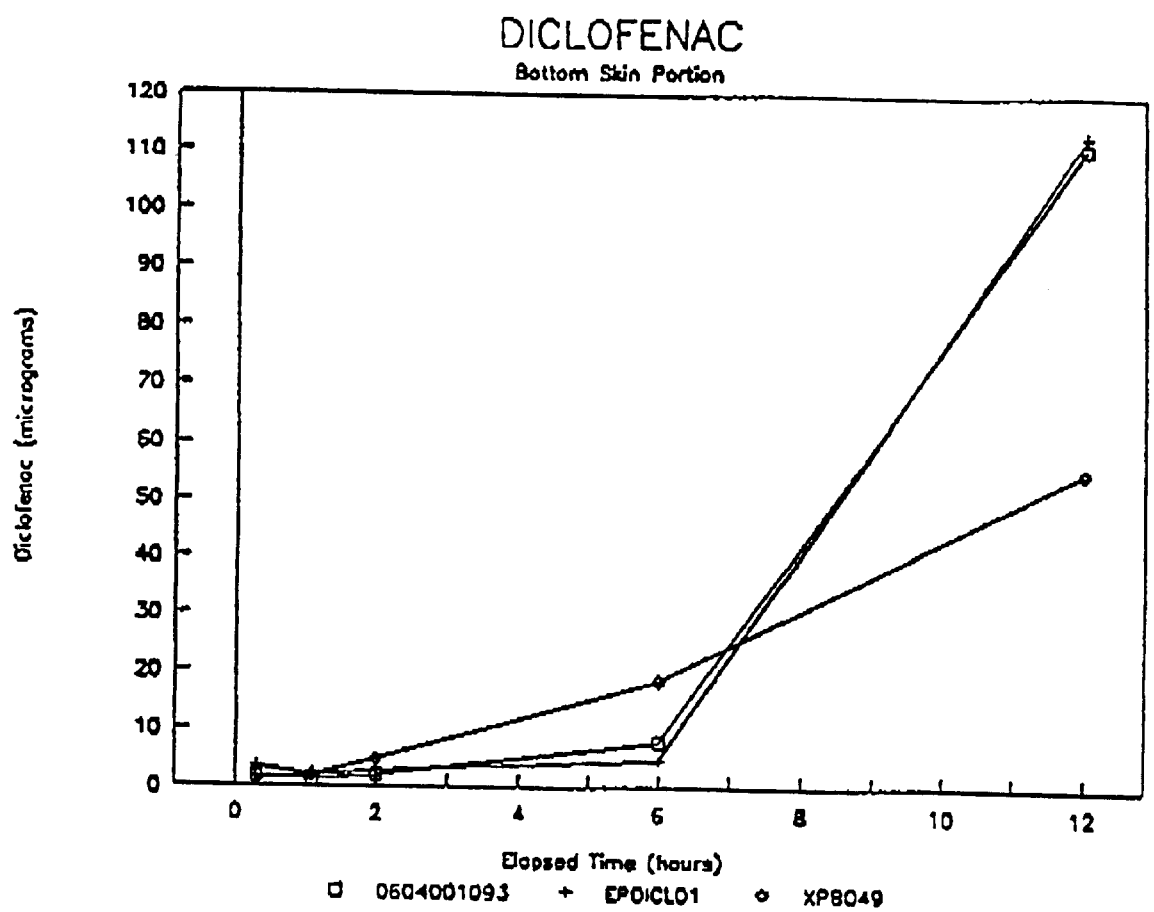
Figure 3:
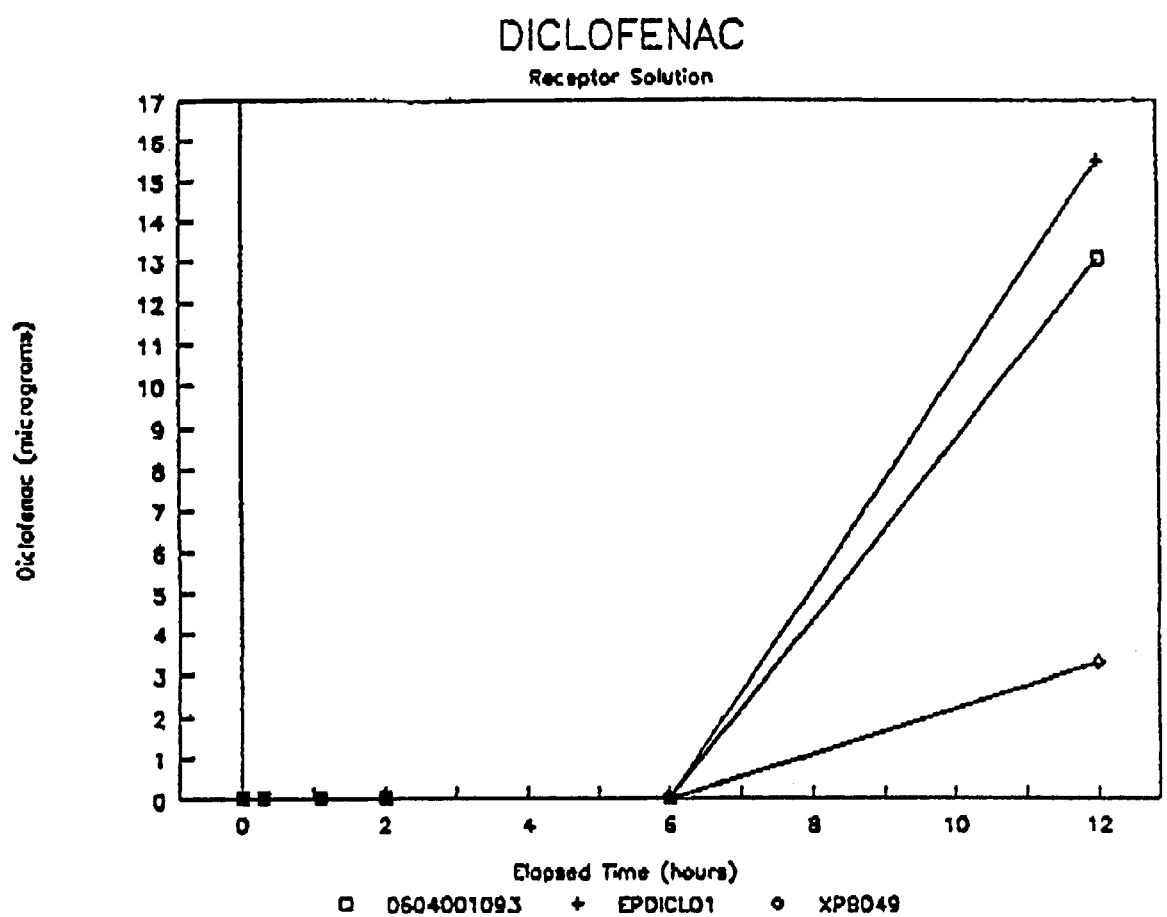

Thus having regard to the above and FIGS. 1, 2 and 3, it is clear that the sodium hyaluronate takes the diclofenac into the skin to the epidermis level (See FIG. 1) more rapidly than the Voltarol Emugel or non-hyaluronic acid diclofenac containing control formulation and retains it there longer. The other formulations take the NSAID, diclofenac, through the bottom skin portion (dermis) quicker, thereby clearing it from the epidermis and dermis, quicker. Furthermore, more of Applicants' formulation is in the epidermis and in the dermis even after 12 hours.

It is also clear that Applicants' formulations clear into the lymphatic system not through the blood system. Yet the prior art topical formulations have always tried "to drive" the formulations through the skin into the blood for treatment of the disease or condition in the area (i.e. systemic action).

Thus, our formulation and combination, penetrates quickly and rapidly at the site of treatment through the upper skin into the epidermis, where the paccinian bundles are located and retain the NSAID and the form of hyaluronic acid longer, where needed (for example for the treatment of basal cell carcinoma).

Further, the NSAIDs are retained in the area to be treated with the form of hyaluronic acid. In doing so, they preclude prostaglandin synthesis and, in effect, deactivate the synthesis or inhibit synthesis of prostaglandins, permitting the macrophages' scavenger cell activity to eliminate the tumour and lesion. Additionally, a rapid onset of pain relief (analgesic effect) is provided. However, there are no blood levels of the NSAID in the immediate area of treatment. The forms of hyaluronic acid, Applicants believe, are cleared via the lymphatic system. Then the lymphatics pass the forms of yaluronic acid, Applicants believe, to the blood system. Thus, he NSAIDs and forms of hyaluronic acid stay at the site to be treated for well in excess of 12–24 hours, a protracted stay.

Thus, over the period of treatment (for example, application 3 times a day for 2–4 weeks) the NSAIDs penetrate sufficiently to inhibit prostaglandin synthesis to enable macrophages to "scavenge" the tumour cells and eliminate them. The end result is the successful treatment of the disease or condition of the skin or exposed tissue for example the resolution of the basal cell carcinoma, the precancerous, often recurrent, actinic keratoses lesions, fungal lesions, "liver" spots and like lesions (found for the most part in the epidermis), squamous cell tumours, metastatic cancer of the breast to the skin, primary and metastatic melanoma in the skin, genital warts cervical cancer, and HPV (Human Papilloma Virus) including HPV of the cervix, psoriasis (both plaque-type psoriasis and nail bed psoriasis), corns on the feet and hair loss on the head of pregnant women, with complete disappearance of the disease or condition as the case may be, by topical therapy without resorting to surgery.

One of the formulations which we have employed successfully is a gel formulation comprising 3% diclofenac in 2.5% sodium hyaluronate formulated as follows:

| Formulation 1 (3000 ml.) | | | | |
|---|---|---|---|---|
| Formula | Supplier | (LOT) | Amount | Percent |
| Glycerine | Life | 1043 | 150 g (119 ml) | 5 |
| Benzyl Alcohol | Caledon | 02517 | 90 g (86 ml) | 3 |
| Diclofenac Sodium | Prosintex | 9113003 | 90 grams | 3 |
| Sodium Hyaluronate (MW 661,666) | Skymark | HG1003 | 75 grams | 2.5 |
| Sterile water | Baxter | AW4455 | 2795 ml. | balance |

Procedure set up stirring apparatus using a 4 litre stainless steel beaker add water, Glycerine, and Benzyl Alcohol; stir to mix add Diclofenac Sodium and stir for 30 minutes then add the Sodium Hyaluronate and stir for 90 minutes initially, stir at a high torque but avoid splashing; as the gel thickens, stir at a lower torque Another such formulation is:

| Formulation 2 | | | | |
|---|---|---|---|---|
| Formula | Supplier | (LOT) | Amount | Percent |
| Methoxypolyethylene Glycol 350 | Sigma | 34F-0266 | 300 g. | 20 |
| Benzyl Alcohol | BDH | 23797 | 15 g. | 1 |
| Diclofenac Sodium | Prosintex | 9123012 | 45 g. | 3 |
| Sodium Hyaluronate (MW 679,000) | Skymart | HG 1004 | 37.5 g. | 2.5 |
| Sterile Water | Baxter | AW45R6 | 1200 ml. | balance |

Procedure set up stirring apparatus using a 3 litre stainless steel beaker add water, Methoxypolyethylene Glycol 350, and Benzyl Alcohol and stir for 20 minutes to mix add Diclofenac Sodium and stir for 30 minutes to dissolve add Hyaluronate Sodium slowly and stir initially at a high speed, but avoid splashing after addition, stir at a slower speed for 90 minutes; the slower speed reduces the formation of air bubbles the result is a clear, transparent, viscous gel Still other formulations are:

| Formulation 3 3% Diclofenac in 2.5% HA Gel | | | | |
|---|---|---|---|---|
| Formula | Supplier | LOT | Amount | Percent |
| Sterile Water | Baxter | AW45K6 | 1200 ml | — |
| Methoxypolyethylene Glycol 350 | Sigma | 34F-0266 | 300 G (273 ml) | 20% |
| Benzyl Alcohol | BDH | 23797 | 15 G (14 ml) | 1% |
| Diclofenac Sodium | Prosintex | 9123012 | 45 g | 3% |
| Sodium Hyaluronate MW 679,000 | Skymart | HG 1004 | 37.5 g | 2.5% |

Procedure

Set up stirring apparatus using a 2 liter stainless steel beaker,

Add water, Methoxypolyethylene Glycol 350, and Benzyl Alcohol and stir for 20 minutes to mix, Add Diclofenoc Sodium and stir for 30 minutes to disolve, Add Hyularonate Sodium slowly and stir initially at a high speed, but avoid splashing, After addition, stir at a slower speed for 90 minutes, the slower speed reduces the formation of air bubbles, The results is a clear transparent, viscous gel.

| Formulation 4 5% IBUPROFEN IN 3.0% HA GEL, 50 ml JAR | | | | |
|---|---|---|---|---|
| Formula | Supplier | TOT | Amount | Percent |
| Sterile Water | Baxter | AW45R6 | 196 ml | — |
| Meglumine | Falk | 15684 | 11 g | 5.5% |
| Ibuprofen | BDH | 19/241 | 10 g | 5% |
| Benzy Alcohol | BDH | 23797 | 2 g | 1% |
| Glycerin | BDH | 2579 | 2 g | 1% |
| Hyaluronate Sodium Mol Wt 661,600 | Skymart | HG 1003 | 6 g | 3% |

Procedure

Set up stirring apparatus using a 300 ml stainless steel beaker,

Add Steril Water and Meglumine, and stir for 10 minutes,

Add Ibuprofen and stir for 15 minutes,

Add Benzyl Alcohol, followed by Glycerin and stir for 15 minutes,

Finally, add Hyaluronate Sodium slowly and stir initially at a high torque to mix, but avoid splashing, As the gel thickens, stir at a slow speed for 90 minutes.

| Formulation 5 2% PIROXICAM IN 2.5% HA GEL | | | | |
|---|---|---|---|---|
| Formula | Supplier | TOT | Amount | Percent |
| Sterile Water | Baxter | AW45R6 | 200 ml | — |
| Meglumine | Falk | 15684 | 8 g | 4% |
| Piroxicam | AMSA | 1-010 | 4 g | 2% |
| Hyaluronate Sodium MW 661,600 | Skymart | HG 1003 | 5 g | 2.5% |

Procedure

Set up stirring apparatus using a 300 ml stainless steel beaker,

Add 200 ml of sterile water,
Add 8 grams of Meglumine and dissolve,
Very slowly add 4 grams of Piroxicam and stir for 20 minutes,
Slowly add 5 grams of Hyaluronate Sodium and stir at high target,
Stir for 90 minutes at a slower speed Comments A clear yellowish transparent gel Formulation 6
5% IBUPROFEN CREAM, 50 ml JAR

| Formula | Supplier | LOT | Amount | Percent |
|---|---|---|---|---|
| OILY PHASE | | | | |
| Liquid wax DICDD | Brooks | L-1424 | 450 g | 15% |
| Brookswax D | Brooks | P-490 | 480 g | 16% |
| Glycerin | BDH | 109109/2578 | 150 g (119 ml) | 5% |
| AQUEOUS PHASE | | | | |
| Sterile Water | Baxter | AW45F1 | 1950 ml | — |
| Meglumine | Falk | 15684 | 150 g | 5% |
| Ibuprofen MW 200,000 | BKH | 19/241 | 150 g | 5% |
| Sodium Hyaluronate | Skymart | Q01 | 45 g | 1.5% |
| Preservative Suttocide A | Sutton | SH-107 | 9 g | 0.3% |

Procedure

A—Add all the ingredients of the oily phase A into a 4 liter stainless steel beaker, melt at 55° C., finally heat to 75% when Aqueous Phase B is ready B—Into a 3 liter stainless stell beaker, add 1950 ml water, set up, the stirring apparatus, add the Meglumine, stir to dissolve for 10 minutes, Slowly add Ibuprofen, stir to dissolve for 20 minutes, Very slowly add Sodium Hyaluronate and stir colf for one hour to dissolve all the Sodium Hyaluronate, Finally, heat to 75° C., with stirring for a total time of 30 minutes, Pour B into A, both at a temperature of 75° C., slowly Remove the heat source and stir with a strong vortex for one hour, When the temperature has cooled down to 45° C. add preservative Suttocide A, Continue stirring at a slower speed until thetemperature is 35° C., At 35° C. remove the propeller, pour into 50 ml jars.

Formulation 7
1% DICLOFENAC IN 3% HA Gel, 50 ml jar
Quantity 3000 ml

| Formula | Supplier | TOT | Amount | Percent |
|---|---|---|---|---|
| Sterile Water | Baxter | AW45R6 | 2796 ml | —% |
| Glycerin | BDH | 2579 | 50 g (71 ml) | 3% |
| Benzyl Alcohol | BDH | 23797 | 45 g (43 ml) | 1.5% |
| Liquid wax DICDD | Brooks | 191-175 | 90 g | 3% |
| Diclofenac Sodium | Prosintex | 9113003 | 30 g | 1% |
| Hyaluronate Sodium MW 679,000 | Skymout | HG 1004 | 90 g | 3% |

Procedure

Set up stirring apparatus using a 4 liter stainless steel beaker.

Add water, Glycerin, Benzyl Alcohol and Liquid wax DICDD and stir to mix thoroughly for 10 minutes Add Diclofenac Sodium and stir for 30 minutes to dissolve.

Slowly add Hyaluronate Sodium, stirring at a high torque initially during addition.

After addition stir at a slower speed for 90 minutes.

A white opaque viscous gel is formed.

Formulation 8
1% DICLOFENAC IN 3.0% HA Gel, 50 ml tube
Quantity 1500 ml

| Formula | Supplier | TOT | Amount | Percent |
|---|---|---|---|---|
| Sterile Water | Baxter | AW45F1 | 1397 ml | —% |
| Glycerin | Life | 1043 | 45 g (36 ml) | 3% |
| Benzyl Alcohol | Caledon | 02517 | 22.5 g (22 ml) | 1.5% |
| Liquid wax DICDD | Brooks | 191-175 | 45 g | 3% |
| Diclofenac Sodium | Prosintex | 9113003 | 15 g | 1% |
| Sodium Hyaluronate Mol. Wt. 661,600 | Skymart | HG 1003 | 45 g | 1% |

Procedure

Set up stirring apparatus using a 3 liter stainless steel beaker.

Add water, Glycerin, Benzyl Alcohol and Liquiwax DICDD, stir to mix for 10 minutes.

Add Diclofenac Sodium and stir for 30 minutes to dissolve.

Add Sodium Hyaluronate and stir for 90 minutes.

Formulation 9
HYANLGESE CREAM (L)
50 ml tube
Quantity 3000 ml

| FORMULA | SUPPT.IF.R | LOT | AMOUNT | PERCENT |
|---|---|---|---|---|
| A. Oily Phase | | | | |
| Liquid Wax DICDD | Brooks/Amisol | | 450 g | 15.0% |
| Brookswax D | Brooks/Amisol | | 480 g | 16.0% |
| Glycerine | Amisol | | 150 g | 5.0% |
| B. Aqueous Phase | | | | |
| Sterile Water | Baxter | AW4YA8 | 1950 ml | —% |
| Meglumlne | Falk | | 150 g | 5.0% |
| Sodium Hyaluronate MW 207,000 | Skymart | PO1 | 45 g | 1.5% |
| Ibuprofen | BDH | | 150 g | 5.0% |
| Suttocide A | Sutton | | 9.0 g | 0.3% |

Procedure

A.—Add all the ingredients of the oily phase into a 4 liter stainless steel beaker, melt at 55° C., finally heat to 75° C. when aqueous phase is ready (at 75° C.) to pour in.

B.—Into another 4 liter stainless steel beaker, add 1950 ml water.

Set up the stirring apparatus and add the Meglumine

Stir to dissolve with high torque, then slowly add Ibuprofen

When the Ibuprofen is dissolved, slowly add Sodium Hyaluronate

Stir cold for one hour to dissolve all the ingredients

Finally heat to 75° C. and stir thoroughly throughout a 30 minute period

Mix B into A
   Slowly pour B into A (both at 75° C.) with stirring
   Immediately remove the hot plate (heat) and stir
   Stir with a strong vortex for one hour
   When the temperature is 45° C., add the preservative Suttocide A
   Stir for about an hour to cool to 35° C.
   At 35° C. remove the propeller and pour into 50 ml tubes
   Pour 50 grams of the cream into each tube 1% BANAMINE IN 2.5% HA GEL
(L) XPB 041 Quantity 3000 ml

| FORMULA | SUPPLIER | TOT | AMOUNT | PERCENT |
|---|---|---|---|---|
| Sterile Water | Boxter | AW4SA2 | 2400 ml | —% |
| Sodium Hyaluronite MW 661,600 | Skymart | HE1003 | 75 g | 2.5% |
| *Banamine, 100 ml vial | Scheing | O CNXB13 | 300 ml | 1% |
| Banamine, 100 ml vial | Scheing | O CNXB12 | 300 ml | 1% |
|  |  |  | 3000 ml |  |

(50 mg/ml) 600 = 30,000 mg
= 30 grams Flunixin in 600 ml
*Banamine contains Flunixin Meglumine (50 mg Flunixin per ml) or 83 mg Flunixin Meglumine Procedure
   Set up stirring apparatus using a 4 liter stainless steel beaker
   Add water, stir with a strong vortex, then add sodium Hyoluronate slowly
   Then immediately add the Banamine, stir the mixture for 4 hours.

One form of hyaluronic acid and/or salts thereof (for example sodium salt) and homologues, analogues, derivatives, complexes, esters, fragments, and sub-units of hyaluronic acid, preferably hyaluronic acid and salts and thereof, suitable for use with Applicant's invention is a fraction supplied by Hyal Pharmaceuticals Limited. One such fraction is a 15 ml vial of Sodium hyaluronate 20mg/ml (300mg/vial—Lot 2F3). The sodium hyaluronate fraction is a 2% solution with a mean average molecular weight of about 225,000. The fraction also contains water q.s. which is triple distilled and sterile in accordance with the U.S.P. for injection formulations. The vials of hyaluronic acid and/or salts thereof may be carried in a Type 1 borosilicate glass vial closed by a butyl stopper which does not react with the contents of the vial.

The fraction of hyaluronic acid and/or salts thereof (for example sodium salt) and homologues, analogues, derivatives, complexes, esters, fragments, and sub-units of hyaluronic acid, preferably hyaluronic acid and salts thereof, may comprise hyaluronic acid and/or salts thereof having the following characteristics:
   a purified, substantially pyrogen-free fraction of hyaluronic acid obtained from a natural source having at least one characteristic selected from the group consisting of the following:
   i) a molecular weight within the range of 150,000–225,000;
   ii) less than about 1.25% sulphated mucopolysaccharides on a total weight basis;
   iii) less than about 0.6% protein on a total weight basis;
   iv) less than about 150 ppm iron on a total weight basis;
   v) less than about 15 ppm lead on a total weight basis;
   vi) less than 0.0025% glucosamine;
   vii) less than 0.025% glucuronic acid;
   viii) less than 0.025% N-acetylglucosamine;
   ix) less than 0.0025% amino acids;
   x) a UV extinction coefficient at 257 nm of less than about 0.275;
   xi) a UV extinction coefficient at 280 nm of less than about 0.25; and
   xii) a pH within the range of 7.3–7.9. Preferably, the hyaluronic acid is mixed with water and the fraction of hyaluronic acid has a mean average molecular weight within the range of 150,000–225,000. More preferably, the fraction of hyaluronic acid comprises at least one characteristic selected from the group consisting of the following characteristics:
   i) less than about 1% sulphated mucopolysaccharides on a total weight basis;
   ii) less than about 0.4% protein on a total weight basis;
   iii) less than about 100 ppm iron on a total weight basis;
   iv) less than about 10 ppm lead on a total weight basis;
   v) less than 0.00166% glucosamine;
   vi) less than 0.0166% glucuronic acid;
   vii) less than 0.0166% N-acetylglucosamine;
   viii) less than 0.00166% amino acids;
   x) a UV extinction coefficient at 257 nm of less than about 0.23;
   xi) a UV extinction coefficient at 280 nm of less than 0.19; and
   xii) a pH within the range of 7.5–7.7

Other forms of hyaluronic acid and/or its salts, and homologues, derivatives, complexes, esters, fragments and sub units of hyaluronic acid may be chosen from other suppliers, for example those described in the prior art documents. In addition, Applicants have successfully employed sodium hyaluronate produced and supplied by LifeCore™ Biomedical, Inc., having the following specifications:

| Characteristics | Specification |
|---|---|
| Appearance | White to cream colored particles |
| Odor | No perceptible odor |
| Viscosity Average Molecular Weight | <750,000 Daltons |
| UV/Vis Scan, 190–820 nm | Matches reference scan |
| OD, 260 nm | <0.25 OD units |
| Hyaluronidase Sensitivity | Positive response |
| IR Scan | Matches reference |
| pH, 10 mg/g solution | 6.2–7.8 |
| Water | 8% maximum |
| Protein | <0.3 mcg/mg NaHy |
| Acetate | <10.0 mcg/mg NaHy |

| Heavy Metals, maximum ppm | | | | | | | | |
|---|---|---|---|---|---|---|---|---|
| As | Cd | Cr | Co | Cu | Fe | Pb | Hg | Ni |
| 2.0 | 5.0 | 5.0 | 10.0 | 10.0 | 25.0 | 10.0 | 10.0 | 5.0 |

| | |
|---|---|
| Microbial Bioburden | None observed |
| Endotoxin | <0.07 EU/mg NaHy |
| Biological Safety Testing | Passes Rabbit Ocular Toxicity Test |

Another form of sodium hyaluronate is sold under the name Hyaluronan HA-M5070 by Skymart Enterprises, Inc. having the following specifications:

| Specifications' Test Results | |
| --- | --- |
| Lot No. | HG1004 |
| pH | 6.12 |
| Condroitin Sulfate | not detected |
| Protein | 0.05% |
| Heavy Metals | Not more than 20 ppm |
| Arsenic | Not more than 2 ppm |
| Loss on Drying | 2.07% |
| Residue on Ignition | 16.69% |
| Intrinsic Viscosity | 12.75 dl/s (XW: 679,000) |
| Nitrogen | 3.14% |
| Assay | 104.1% |
| Microbiological Counts | 80/g |
| E. coli | Negative |
| Mold and Yeast | Not more than 50/g |

The following references teach hyaluronic acid, sources thereof, and processes of the manufacture and recovery thereof.

U.S. Pat. No. 4,141,973 teaches hyaluronic acid fractions (including sodium salts) having:

"(a) an average molecular weight greater than about 750,000, preferably greater than about 1,200,000—that is, a limiting viscosity number greater than about 1400 $cm^3/g.$, and preferably greater than about 2000 $cm^3/g.$;

(b) a protein content of less than 0.5% by weight;

(c) ultraviolet light absorbance of a 1% solution of sodium hyaluronate of less than 3.0 at 257 nanometers wavelength and less than 2.0 at 280 nanometers wavelength;

(d) a kinematic viscosity of a 1% solution of sodium hyaluronate in physiological buffer greater than about 1000 centistokes, preferably greater than 10,000 centistokes;

(e) a molar optical rotation of a 0.1–0.2% sodium hyaluronate solution in physiological buffer of less than $-11 \times 10^3$ degree—$cm^2$/mole (of disaccharide) measured at 220 nanometers;

(f) no significant cellular infiltration of the vitreous and anterior chamber, no flare in the aqueous humour, no haze or flare in the vitreous, and no pathological changes to the cornea, lens, iris, retina, and choroid of the owl monkey eye when one milliliter of a 1% solution of sodium hyaluronate dissolved in physiological buffer is implanted in the vitreous replacing approximately one-half the existing liquid vitreous, said HUA being (g) sterile and pyrogen free and (h) non-antigenic."

Canadian Letters Patent 1,205,031 (which refers to U.S. Pat. No. 4,141,973 as prior art) refers to hyaluronic acid fractions having average molecular weights of from 50,000 to 100,000; 250,000 to 350,000; and 500,000 to 730,000 and discusses processes of their manufacture.

In order to determine the blood levels in patients using formulations made according to embodiments of the invention, a study of the pharmacokinetic profiles of two topical diclofenac formulations after repeat dosing were undertaken.

One such product was the product Voltarol Emulgel marketed in the United Kingdom by Geigy. The other was a Diclofenac preparation in Hyaluronic Acid.

This was an open, repeat dose, crossover comparison using a randomized balanced block in six healthy volunteers.

The study consisted of administration with one, two week period in between periods, each period lasting fourteen days. The test articles applied were for the first six days of each period and the seventh day was study day during which the final application is made and blood samples taken.

The approximate duration of the study including pre and post study screening was six weeks.

Doses

Diclofenac with Hyaluronic Acid Dose: Approximately 2 g, three times daily Route: Topical (W1) Voltarol Emulgel, Diclofenac diethylammonium salt 1.16 g aqueous gel (Geigy) Dose: Approximately 2 g, three times daily Route: Topical (W1)

ADMINISTRATION: to suitable patients

Subjects applied one of the designated test articles topically to the calves and massaged into the skin, in a dose of approximately 2 g per application three times a day for six consecutive days. The size of a 2 g dose was prepared by comparison with a silicone example given to each subject.

On the seventh day, the cream was applied once, in the same manner as before, under the supervision of the staff of the Clinical Investigation Unit.

After a washout period of one week the procedure was repeated with the alternate test article.

The following were the results of the tests:

(H = hyaluronic acid formulation)
(V = Voltarol Emulgel)
All concentrations ng $ml^{-1}$

| | TIME POINT (hours) | | | | | | | | | | | |
| --- | --- | --- | --- | --- | --- | --- | --- | --- | --- | --- | --- | --- |
| SUBJECT | 0 | 0.25 | 0.5 | 1 | 2 | 3 | 4 | 5 | 6 | 8 | 10 | 12 |
| | PERIOD I | | | | | | | | | | | |
| H-1 | 10.3 | 7.1 | 6.4 | ND | ND | 5.4 | 6.5 | 5.1 | ND | ND | ND | ND |
| H-2 | ND | 5.1 | ND | 5.1 | ND | ND | ND | ND | ND | 5.1 | ND | ND |
| V-3 | ND | ND | ND | 5.5 | 5.2 | ND | ND | ND | ND | ND | ND | ND |
| H-4 | ND | ND | ND | ND | ND | ND | ND | ND | ND | ND | ND | ND |
| V-5 | ND | ND | ND | ND | ND | ND | ND | ND | ND | ND | ND | ND |
| V-6 | ND | ND | ND | ND | ND | ND | ND | 8.4 | ND | ND | ND | ND |
| | PERIOD II | | | | | | | | | | | |
| V-1 | ND | ND | ND | ND | ND | ND | ND | ND | ND | ND | ND | ND |
| V-2 | ND | ND | ND | ND | ND | ND | ND | ND | ND | ND | ND | ND |

-continued (H = hyaluronic acid formulation)
(V = Voltarol Emulgel)
All concentrations ng ml$^{-1}$

| | TIME POINT (hours) | | | | | | | | | | | |
|---|---|---|---|---|---|---|---|---|---|---|---|---|
| SUBJECT | 0 | 0.25 | 0.5 | 1 | 2 | 3 | 4 | 5 | 6 | 8 | 10 | 12 |
| H-3 | ND | ND | ND | ND | ND | ND | ND | ND | ND | ND | ND | ND |
| V-4 | ND | ND | ND | ND | ND | ND | ND | ND | ND | ND | ND | ND |
| H-5 | ND | ND | ND | ND | ND | ND | ND | ND | ND | ND | ND | ND |
| H-6 | ND | ND | ND | ND | ND | ND | ND | ND | ND | ND | ND | ND |

ND = NONE DETECTED (>5.0 ng ml$^{-1}$)

Other tests were undertaken to determine blood levels comparing Proflex (a formulation containing Ibuprofen) and the following formulation containing hyaluronic acid and Ibuprofen.

HYANALGESE CREAM (L) X PB 022
−50 ml tube
Quantity 3000 ml

| FORMULA | SUPPLIER | LOT | AMOUNT | PERCENT |
|---|---|---|---|---|
| A. Oil Phase | | | | |
| Liquid Wax DICDD | Brooks/Amisol | | 450 g | 15.0% |
| Brookswax D | Brooks/Amisol | | 480 g | 16.0% |
| Glycerine | Amisol | | 150 g | 5.0% |
| B. Aqueous Phase | | | | |
| Sterile Water | Baxter | AW4YA8 | 1950 ml | —% |
| Meglumine | Falk | | 150 g | 5.0% |
| Sodium Hyaluronate MW 207,000 | Skymart | Po1 | 45 g | 1.5% |
| Ibuprofen | BDH | | 150 g | 5.0% |
| Suttocide A | Sutton | | 9.0 g | 0.3% |

The following were the results

The above clearly indicates that the blood levels are much less using hyaluronic acid to administer the NSAID.

EXAMPLES

The following examples are offered to illustrate uses of Applicants' invention.

Example 1

A male patient had a number of lesions (basal cell carcinoma), including one on his forehead which was a combination of major "horny epithelium" and some degree of ulceration. After continuous treatment with Formulation 1 (several times per day for several weeks), the lesions showed epithelialization, no hemorrhagic areas, and no initiated areas (as they were in the past without our treatment). The "horny epithelium" and ulceration of the forehead lesion were also gone. The patient had a complete successful response with the formulation. All basal cell carcinoma lesions had been resolved and disappeared. There has been no recurrence.

Example 2

60 year old male tennis player had sore elbow and basal cell carcinoma on forearm proximate sore elbow. Patient tried Formulation 1 to abate pain in tennis elbow. (Dr. Falk

| SUBJECT | | Time after administration (Hours) | | | | | | | | | | | |
|---|---|---|---|---|---|---|---|---|---|---|---|---|---|
| Number | PD | 0 | 0.25 | 0.5 | 1 | 2 | 3 | 4 | 5 | 6 | 8 | 10 | 12 |
| (A) PROFLEX | | | | | | | | | | | | | |
| 1 | ND | 0.41 | 0.37 | 0.37 | 0.32 | 0.30 | 0.27 | 0.27 | 0.24 | 0.37 | 0.31 | 0.31 | 0.16 |
| 2 | ND | 0.12 | 0.12 | 0.08 | 0.11 | 0.12 | 0.12 | 0.07 | 0.08 | 0.09 | 0.08 | ND | 0.06 |
| 3 | ND | 0.09 | 0.08 | 0.07 | ND | ND | ND | ND | ND | ND | ND | ND | ND |
| 4 | ND | 0.12 | 0.14 | 0.16 | 0.11 | 0.11 | 0.25 | 0.24 | 0.17 | 0.13 | 0.16 | 0.11 | 0.13 |
| 5 | ND | 0.14 | 0.19 | 0.19 | 0.15 | 0.16 | 0.16 | 0.14 | 0.12 | 0.11 | 0.13 | 0.10 | 0.07 |
| 6 | ND | 0.11 | 0.09 | 0.09 | 0.06 | 0.07 | 0.05 | 0.05 | 0.05 | 0.05 | 0.05 | ND | ND |
| Mean | 0.00 | 0.17 | 0.17 | 0.16 | 0.13 | 0.13 | 0.14 | 0.13 | 0.11 | 0.12 | 0.11 | 0.09 | 0.07 |
| S.D. | 0.00 | 0.12 | 0.10 | 0.11 | 0.10 | 0.10 | 0.10 | 0.10 | 0.08 | 0.13 | 0.11 | 0.12 | 0.06 |
| (B) HYALURONIC ACID AND IBUPROFEN | | | | | | | | | | | | | |
| 1 | ND | 0.11 | 0.11 | 0.12 | 0.08 | 0.08 | 0.09 | 0.11 | 0.12 | 0.08 | 0.11 | 0.16 | 0.14 |
| 2 | ND | 0.22 | 0.21 | 0.26 | 0.17 | 0.24 | 0.24 | 0.25 | 0.23 | 0.19 | 0.19 | 0.20 | 0.14 |
| 3 | ND | 0.17 | 0.10 | 0.12 | 0.09 | 0.08 | 0.07 | 0.06 | ND | 0.06 | 0.26 | 0.09 | 0.05 |
| 4 | ND | ND | ND | ND | ND | ND | ND | ND | ND | ND | ND | ND | ND |
| 5 | ND | 0.17 | 0.16 | 0.16 | 0.12 | 0.09 | 0.10 | 0.11 | 0.10 | 0.09 | 0.10 | 0.07 | ND |
| 6 | ND | 0.07 | 0.07 | 0.09 | ND | ND | ND | ND | ND | ND | ND | ND | ND |
| Mean | 0.00 | 0.12 | 0.11 | 0.13 | 0.08 | 0.08 | 0.08 | 0.09 | 0.08 | 0.07 | 0.11 | 0.09 | 0.06 |
| S.D. | 0.00 | 0.08 | 0.07 | 0.08 | 0.06 | 0.08 | 0.08 | 0.09 | 0.09 | 0.07 | 0.10 | 0.08 | 0.07 |

ND None detected <0.05 μg/ml was not treating this patient for anything at the time and merely offered the formulation for pain relief of the elbow.) However, the formulation "spilled" over onto the Patient's basal cell carcinoma. Patient was planning to have basal cell carcinoma removed surgically by another doctor, but when he came in to see the doctor, the basal cell carcinoma was disappearing (because of spill-over of Formulation 1). Treatment was now undertaken by Dr. Falk with direct application of Formulation 1 to the lesion 3 times a week for two additional weeks. After two weeks, the basal cell carcinoma disappeared. There has been no recurrence.

Example 3

Male, mid to late 40's had severe basal cell carcinoma on left temple. Doctors recommended its removal by surgery. However, the surgery would have been risky because of the lesion's proximity to facial nerves.

Patient saw Dr. Falk who gave him Formulation 2 to be applied 3 times daily.

After 14 days, 75% of the lesion was gone. Surgery was postponed and the treatment was continued. Application of Formulation 2 continued for an additional two weeks. At the end of the 2-week period, the lesion was completely resolved and disappeared without any surgery being required. There has been no recurrence.

Example 4

Male, early 40's, had recurrent actinic keratoses lesion on his right temple. Early attempts at removal by third parties involved the application of liquid nitrogen (twice) without final resolution. The lesion kept recurring. The patient was sent to Dr. Falk who treated the lesion with Formulation 1 with applications 3 times daily for 7 days. After 7 days, the lesion was completely resolved with no subsequent recurrence.

Example 5

A male patient suffering from kyphosis suffered from constant back pain. Taking analgesics orally and rubbing back preparations onto his back did little to alleviate the back pain. When NSAIDs in hyaluronic acid (sodium hyaluronate) were applied directly to the back, the back pain eased and disappeared.

With indomethacin (dissolved in N-methyl glucamine) and naproxen both dissolved in hyaluronic acid, the patient experienced some side effects. However, with Toradol™ (the [±] form tromethamine salt of ketorolac—a prostaglandin biosynthesis inhibitor and analgesic and anti-inflammatory, the back pain eased and disappeared for some time and there were no side effects.

Example 6

A male patient with basal cell carcinoma was first treated by an oncologist who attempted to surgically excise the lesion (without success) and then irradiated the lesion again without success. The patient then attended before Dr. Falk who applied Applicant's formulation (diclofenac with sodium hyaluronate and excipients). Application was made three times daily for about a month and the lesion disappeared. Some excoriation anterior and slightly superior developed over the last two weeks but was cleared by the application of hyaluronic acid by itself.

This resolution clearly indicates that even with prior applications of unsuccessful therapies (surgery and irradiation), Applicant's formulations can be used successfully.

Example 7

In another patient, a drug (methotrexate) was carried in hyaluronic acid and applied topically to a patient with psoriasis. The formulation was absorbed and the psoriasis cleared.

Example 8

A patient with dermal (skin) metastases in a fibratic scar form and metastatic cancer in the form of musculoskeletal involvement in her thorax.

On topical application of our formulation comprising diclofenac (Voltaren) in hyaluronic acid (sodium hyaluronate), her pain decreased dramatically and her skin and boney involvements steadily improved.

As many changes can be made to the invention without departing from the scope of the invention, it is intended that all material contained herein be interpreted as illustrative of the invention and not in a limiting sense.

The embodiments of the invention in which an exclusive property of privilege is claimed are as follows:

1. A method of accumulating a drug and a form of hyaluronic acid in the skin or exposed tissue comprising topically administering a dosage of a pharmaceutical composition comprising together with pharmaceutical excipients suitable for topical application, a therapeutically effective, to treat and resolve a disease or condition of the skin and exposed tissue selected from the group consisting of basal cell carcinoma and actinic keratoses and pain, non-toxic amount of a drug and an effective non-toxic dosage amount of a form of hyaluronic acid selected from the group consisting of hyaluronic acid and pharmaceutically acceptable salts thereof sufficient to facilitate the drug's quick penetration to the site in the skin or tissue of the disease or condition to accumulate and remain in the epidermis for a prolonged period of time wherein the percentage of the dosage of the form of the hyaluronic acid is between 1–3% by weight of the dosage and has a molecular weight less than 750,000 daltons but greater than 150,000 daltons and the percent of the drug of the composition is between 1–5% by weight of the dosage.

2. The method of claim 1 where the accumulation takes place in the epidermis.

3. The method of claim 1 or 2 wherein the form of hyaluronic acid is sodium hyaluronate.

4. A method of quickly delivering a drug to the epidermis and maintaining the drug therein for a prolonged period of time, the method comprising topically administering a dosage of a pharmaceutical composition comprising together with pharmaceutical excipients suitable for topical application, a therapeutically effective, to treat and resolve a disease a condition of the skin and exposed tissue selected from the group consisting of basal cell carcinoma and actinic keratoses, non-toxic amount of a drug which blocks prostaglandin synthesis and an amount of a form of hyaluronic acid selected from hyaluronic acid and pharmaceutically acceptable salts thereof sufficient to facilitate the drug's quick penetration to the site in the skin or tissue of the disease or condition through the tissue to accumulate and remain in the epidermis for a prolonged period of time to block prostaglandin synthesis wherein the percentage of the dosage of the form of the hyaluronic acid is between 1–3% by weight of the dosage and has a molecular weight less than 750,000 daltons but greater than 150,000 daltons and the percent of the drug of the composition is between 1–5% by weight of the dosage.

5. The method of claim 4, wherein accumulation takes place in the epidermis.

6. The method of claim 4 wherein the form of hyaluronic acid is sodium hyaluronate.

7. The method of claim 6 wherein the drug is a non-steroidal anti-inflammatory drug (NSAID).

8. The method of claim 7 wherein the NSAID is selected from diclofenac, indomethacin, naproxen, and (+,-) tromethamine salt of ketorolac.

9. The method of claim 7 wherein the NSAID is selected from Ibuprofen piroxicam, acetylsalicylic acid, propionic acid derivatives and flunixin.

10. A method of controlling the unloading of a drug from the skin or exposed tissue of a human suffering trauma or pathology into the lymphatic system comprising transporting into the skin or exposed tissue an amount of a drug by an effective non-toxic dosage amount of a form of hyaluronic acid selected from the group consisting of hyaluronic acid and pharmaceutically acceptable salts thereof wherein the percentage of the dosage of the form of hyaluronic acid is between 1–3% by weight and has a molecular weight less than 750,000 daltons but greater than 150,000 daltons and the percent of the drug is between 1–5% by weight.

11. The method of claim 10 wherein the form of hyaluronic acid is sodium hyaluronate.

12. The method of claim 11 wherein the drug is a drug which inhibits prostaglandin synthesis.

13. The method of claim 12 wherein the drug is a non-steroidal anti-inflammatory drug (NSAID).

14. The method of claim 13 wherein the NSAID is selected from the group consisting of diclofenac, indomethacin, naproxen, (+,−) tromethamine salt of ketorolac, Ibuprofen, piroxicam, acetylsalicylic acid, propionic acid derivatives and flunixin.

15. A method of accumulating a drug in the skin or exposed tissue or both comprising topically administering to the skin or exposed tissue or both, a pharmaceutical composition comprising the drug and a form of hyaluronic acid, the amount of the composition administered comprising an effective non-toxic amount of the drug and an effective non-toxic amount of a form of hyaluronic acid selected from the group consisting of hyaluronic acid and pharmaceutically acceptable salts thereof to transport or facilitate or cause the transport of the drug into the skin or exposed tissue to accumulate in the epidermis wherein the percent of the form of hyaluronic acid is 1–3% by weight of the composition and has a molecular weight less than 750,000 daltons but greater than 150,000 daltons and the percent of the drug is between 1–5% by weight.

16. The method of claim 15 wherein the form of hyaluronic acid is sodium hyaluronate.

17. The method of claim 16 wherein the drug is a drug which inhibits prostaglandin synthesis.

18. The method of claim 17 wherein the drug is a non-steroidal anti-inflammatory drug (NSAID).

19. The method of claim 18 wherein the NSAID is selected from the group consisting of diclofenac, indomethacin, naproxen, (+,−) tromethamine salt of ketorolac, Ibuprofen, piroxicam, acetylsalicylic acid, propionic acid derivatives and flunixin.

* * * * *